United States Patent [19]

Batcho et al.

[11] 4,310,467
[45] Jan. 12, 1982

[54] PROCESS AND INTERMEDIATES FOR THE SYNTHESIS OF VITAMIN D$_3$ METABOLITES

[75] Inventors: Andrew D. Batcho, North Caldwell, N.J.; Donald E. Berger, Jr., Mountain View, Calif.; Milan R. Uskokovic, Upper Montclair, N.J.

[73] Assignee: Hoffmann-La Roche Inc., Nutley, N.J.

[21] Appl. No.: 199,167

[22] Filed: Oct. 22, 1980

[51] Int. Cl.$^3$ ............................................. C07J 9/00
[52] U.S. Cl. .............................. 260/397.5; 260/397.4; 260/239.55 R
[58] Field of Search ................................. 260/397.5; /Steroids MS File

[56] References Cited

U.S. PATENT DOCUMENTS 3,994,934  11/1976  Salmond ........................ 260/397.2
4,193,921  3/1980  Furst et al. ..................... 260/397.2

*Primary Examiner*—Elbert L. Roberts
*Attorney, Agent, or Firm*—Jon S. Saxe; Bernard S. Leon; James H. Callwood

[57] ABSTRACT

The present disclosure is directed to a process and intermediates for the synthesis of Vitamin D$_3$ metabolites such as 1,25-dihydroxycholecalciferol, 25-hydroxycholecalciferol and 24R,25-dihydroxycholecalciferol from 17-keto steroids via intermediates having the natural steroid configuration at the 20-position. These novel intermediates are prepared from 17-keto steroids by reaction with ethyltriphenylphosphonium halides followed by reaction with formaldehyde to form comounds having the natural steroid configuration at the 20-position and which are suitable substrates for the preparation of the aforementioned Vitamin D$_3$ metabolites.

42 Claims, No Drawings

PROCESS AND INTERMEDIATES FOR THE SYNTHESIS OF VITAMIN D₃ METABOLITES

BACKGROUND OF THE INVENTION

The preparation of steroid compounds such as 1α,25-dihydroxycholesterol, 25-hydroxycholesterol and 24R,25-dihydroxycholesterol has involved numerous problems. For example, in the past, it has been necessary to utilize procedures involving numerous preparative steps, thereby resulting in low overall yields of the ultimate product. Additionally, the synthetic procedures have been time-consuming and tedious, involving the need for separation of various products by chromatographic procedures in order to arrive at a substrate having the natural steroid configuration at the 20-position. Because of the foregoing problems, it has heretofore been impractical to prepare compounds of potential commercial importance on a commercially-practical scale.

17-keto steroids, such as dehydroepiandrosterone, are available from microbial degradation of readily-available plant steroids such as sitosterol, campesterol, etc. Thus, the 17-keto steroids are abundantly-available substrates which could provide attractive starting materials for the synthesis of a number of steroid compounds which are of potential commercial importance. However, there has heretofore been no methodology available for the efficient stereospecific introduction of a suitably functionalized side chain at the 17-position having the natural steroid C-20 configuration which would allow for further elaboration of these substrates into commercially-important products.

The ene reaction, which is known in the prior art (see, for example, Blomquist et al., J. Org. Chem. 33:1156 (1967)), involves the addition of a compound with a double bond (enophile) to an olefin possessing an allylic hydrogen (ene) and involves allylic shift of the double bond, transfer of the allylic hydrogen to the enophile and bonding between the two unsaturated termini. It is also known in the prior art that 17-keto steroids may be modified by reaction with an ethyltriphenylphosphonium halide to produce a 17-ethylidene derivative having a Z-double bond configuration.

SUMMARY OF THE INVENTION

In accordance with the present invention, it has been found that 17-keto steroids, once they have been reacted with an ethyltriphenylphosphonium halide via a Wittig reaction to produce ethylidene derivatives of the formula

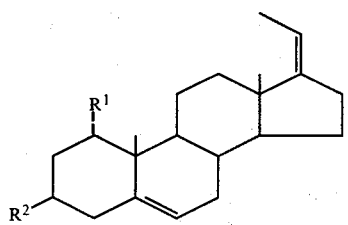

wherein $R^1$ is hydrogen, hydroxy or acyloxy; and $R^2$ is hydroxy or acyloxy,
can be transformed via the ene reaction with formaldehyde, stereospecifically in respect to the C-20 configuration, to a compound with a three-carbon side chain of the formula

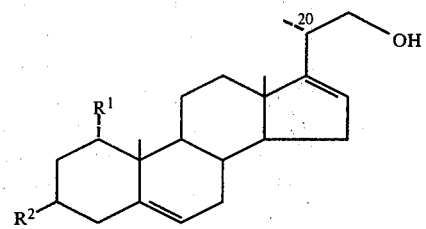

wherein $R^1$ and $R^2$ are as above,
followed by selective hydrogenation of the $\Delta^{16}$ double bond so as to produce a compound of the formula

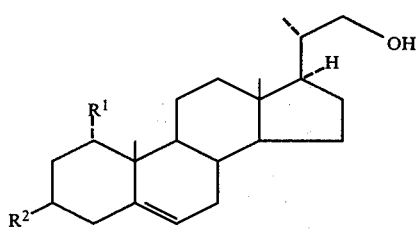

wherein $R^1$ and $R^2$ are as above.

Thus, by the process of the present invention, readily-available 17-keto steroids may be transformed to ethylidene derivatives by prior art procedures to produce a substrate which can be used in the ene reaction to produce steroid molecules having a functionalized three-carbon side chain at the 17-position wherein the methyl group at the 20-position has the natural steroid α-orientation. These intermediates, having the natural steroid configuration, are suitable for further elaboration into Vitamin D₃ metabolites. Thus, by the process of the present invention, the prior art problems involving numerous preparative steps, low yields and tedious separation procedures have been eliminated, and a process is provided for preparing commercially-important products on a commercially-practical scale.

DETAILED DESCRIPTION OF THE INVENTION

As used throughout the specification and the appended claims, the term "lower alkyl" means straight- or branched-chain saturated aliphatic hydrocarbon groups preferably containing 1-7 carbon atoms. Representative of such groups are methyl, ethyl, isopropyl, butyl, pentyl, hexyl, heptyl and octyl. The term "lower alkoxy" means a lower alkyl group attached to the remainder of the molecule by oxygen. Examples of lower alkoxy are methoxy, ethoxy, propoxy, isopropoxy and the like. The term "acyloxy" means the residue of an alkyl or aromatic carboxylic acid formed by the removal of a hydrogen atom from the hydroxyl portion of the carboxyl group. Examples of alkyl carboxylic acids are formic acid, acetic acid, pivalic acid, propionic acid, butyric acid, caproic acid, oenanthic acid, undecylenic acid and oleic acid. Aromatic acyloxy groups are the residue of organic carboxylic acid containing 7-15 carbon aoms such as benzoic acid, phenylacetic acid and the like. The term "aryl" means an organic, aromatic radical derived by the remval of one atom (e.g., phenyl) which can be substituted or unsubstituted by one or more lower alkyl groups (e.g., tolyl). Preferred acyloxy groups are $C_{1-7}$ alkanoyloxy groups, especially acetyloxy. The lower alkanoic acids may be substituted with one or more halo groups. Among the preferred halo substituted lower alkanoyloxy groups are trihaloacetyloxy groups such as trifluoroacyloxy.

In the formulas represented herein, the various substituents are illustrated as joined to the steroid nucleus by one of the following notations: a solid line (—) indicates that a substituent is in the β-orientation (i.e., above the plane of the molecule) and a broken line (- - -) indicates that a substituent is the α-orientation (i.e., below the plane of the molecule).

In the first step of the process of the present invention, 17-keto steroids of the formula

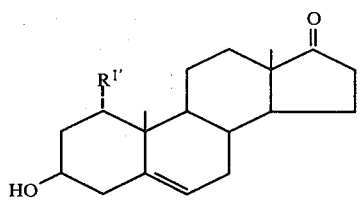

IV wherein $R^{1'}$ is hydrogen or hydroxy, are allowed to react with an ethyltriphenylphosphonium halide via a Wittig reaction in the presence of a strong base so as to produce a compound of the formula

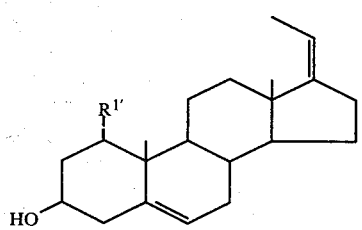

I-A wherein $R^{1'}$ is as above.

The reaction is carried out in an inert organic solvent under an inert atmosphere at reaction temperatures ranging from 0°–150° C. The inert organic solvents which may be used in the present process may be any inert aprotic organic solvent. Exemplary of such solvents are tetrahydrofuran, dimethyl sulfoxide, dimethylformamide, benzene, toluene, hexane and the like. The strong base which may be used is any strong base conventionally known in the art capable of forming a Wittig reagent from an ethyltriphenylphosphonium halide. Exemplary of such strong bases are lower alkali metal salts, for example, butyllithium, alcohol salts such as potassium tertiary-butylate, potassium amylate and the like.

The reaction temperature at which the foregoing reaction can be carried out is not critical and can range from 0°–150° C. with room temperature being preferred.

In the second step of the present invention, the compound of formula

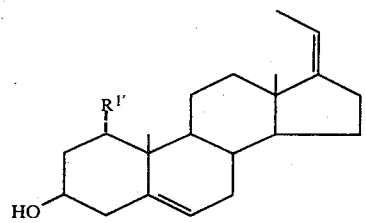

I-A wherein $R^{1'}$ is hydrogen or hydroxy, is allowed to react with formaldehyde or a formaldehyde-producing compound such as paraformaldehyde under conditions hereinafter described to yield a compound of the formula

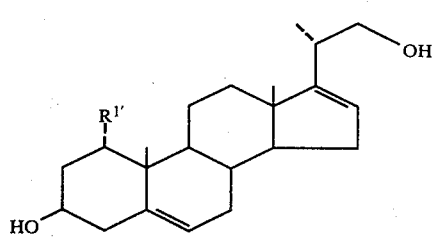

II-A wherein $R^{1'}$ is hydrogen or hydroxy.

The reaction product of formula II-A is then reacted in a hydrogen atmosphere in the presence of a hydrogenation catalyst under conditions hereinafter described to yield a compound of the formula

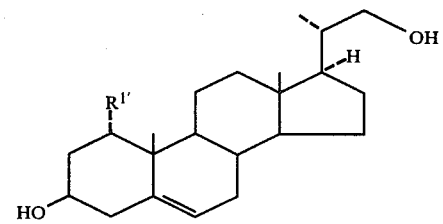

III-A wherein $R^{1'}$ is as above.

If it is desired to produce the compound of formula I-B

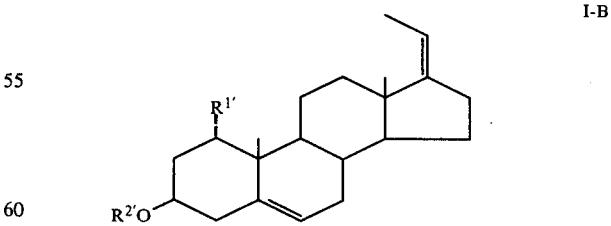

I-B wherein $R^{1'}$ is hydrogen or hydroxy; and $R^{2'}$ is acyl, the compound of formula I-A is reacted with 1 mole of an acylating agent. One mole of an acylating agent will selectively acylate the hydroxy group at position 3.

If it is desired to produce a compound of formula I-C

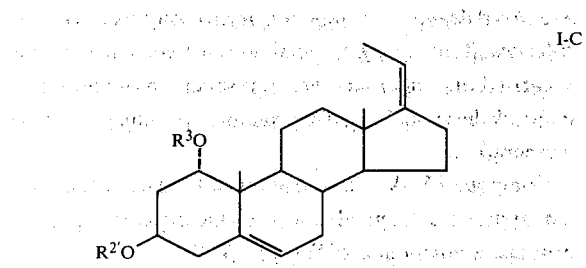

wherein $R^3$ and $R^{2'}$ are both acyl, the compound of formula I-A, wherein $R^{1'}$ is hydroxy, is reacted with 2 moles of an acylating agent so as to acylate the hydroxy groups at the 1- and 3-positions. When 2 moles of an acylating agent are reacted with a compound having hydroxy groups at the 1- and 3-positions, both hydroxy groups are converted to acyloxy groups.

Exemplary of suitable acylating agents are lower alkyl carboxylic acid anhydrides, for example, acetic anhydride and trifluoroacetic anhydride; aromatic anhydrides, for example, benzoic anhydride, nitrobenzoic anhydride, toluic anhydride and the like. The acylating agent is added in the presence of a weak base such as pyridine, dimethylaniline, triethylamine, sodium acetate and the like. Dimethylaminopyridine may optionally be added to catalyze the reaction.

If it is desired to produce a compound of the formula

I-D wherein $R^{2'}$ is hydrogen; and $R^4$ is acyloxy, the compound of formula I-C may be reacted with 1 mole of a base at reflux conditions. The acyl group at $R^{2'}$ will be hydrolyzed, thereby selectively removing the acyl protecting group at the 3-position.

In the second and key step of the present invention, the compound of formula I

I wherein $R^1$ is hydrogen, hydroxy or acyloxy; and $R^2$ is hydroxy or acyloxy, is allowed to react with formaldehyde or a formaldehyde-producing compound such as paraformaldehyde via the ene reaction so as to produce a compound of the formula

II wherein $R^1$ and $R^2$ are as above.

This reaction is carried out in any conventional inert solvent; for example, methylene chloride, carbon tetrachloride, chloroform, aromatic hydrocarbons such as benzene, toluene and the like, and lower aliphatic hydrocarbons such as hexane, octane and the like. The reaction may also be carried out in aqueous systems using protic acids. The reaction is carried out at temperatures ranging from $-20°$ to $45°$ C., the particular reaction temperature not being critical. The reaction is catalyzed by Lewis and protic acids such as boron trifluoride etherate, aluminum chloride, methanesulfonic acid, trifluoroacetic acid and the like.

The compound of formula II is reacted in a hydrogen atmosphere in the presence of a hydrogenation catalyst thereby selectively hydrogenating the $\Delta^{16}$ double bond so as to produce a compound of the formula

III wherein $R^1$ and $R^2$ are as above.

Preferred hydrogenation catalysts are platinum on charcoal, platinum oxide and Raney nickel. The reaction is carried out in an inert solvent under a hydrogen atmosphere at temperatures ranging from $0°$ to $40°$ C., preferably $23°$ C.

Or, alternatively, side chain containing an acyloxy group may be stereoselectively introduced directly into the C-20 position by reacting the compound of formula I

I wherein $R^1$ and $R^2$ are as above, with formaldehyde or a compound capable of generating formaldehyde in situ such as paraformaldehyde via the ene reaction in the presence of an acylating agent in the presence of a Lewis or protic acid so as to produce a compound of the formula

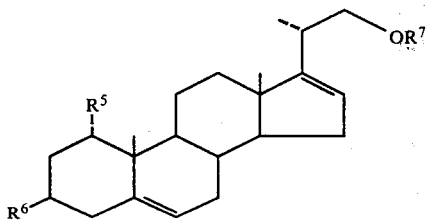

wherein $R^5$ is hydrogen or acyloxy; $R^6$ is acyloxy; and $R^7$ is acyl.

The $\Delta^{16}$ double bond in the compound of formula II-B is catalytically hydrogenated in the presence of a conventional hydrogenation catalyst and a hydrogen atmosphere so as to produce a compound of formula III-B

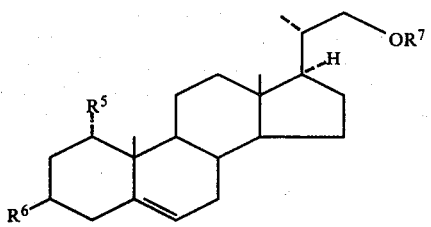

wherein $R^5$ is hydrogen or acyloxy; $R^6$ is acyloxy; and $R^7$ is acyl.

Representative of hydrogenation catalysts are platinum, Raney nickel or any conventional metal catalyst. The hydrogenation can be carried out at temperatures ranging from 0° to 40° C., preferably 20° C.

In an alternative embodiment of the present invention, the compound of the formula

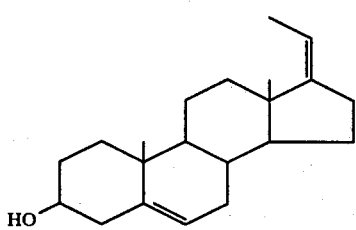

is transformed into a compound of formula V-A

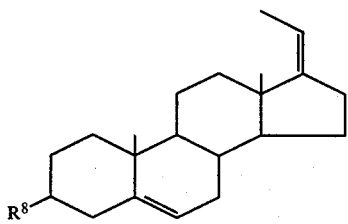

wherein $R^8$ is a conventional leaving group.

Any method of converting a hydroxy group to a more reactive leaving group may be utilized to effect this transformation. Any conventional leaving group can be used in the compound of formula V-A. Exemplary of such leaving groups are groups well known in the art which can easily be removed such as halides, lower alkylsulfonyloxy, arylsulfonyloxy and the like.

Preferred leaving groups are arylsulfonyloxy with p-toluenesulfonyl being especially preferred. The reaction is carried out under an inert atmosphere in the presence of weak base such as, for example, pyridine at room temperature.

Compound V-A is in turn allowed to react with formaldehyde or a formaldehyde-producing compound to produce a compound of formula V-B

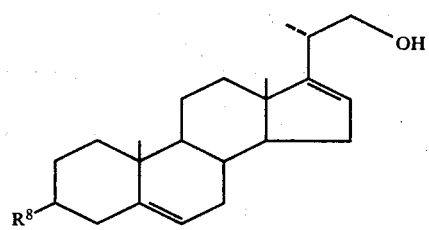

wherein $R^8$ is as above.

The reaction is carried out as described in connection with the formation of compound II as previously described.

Alternatively, the foregoing reaction may be carried out in the presence of an acylating agent to produce the compound of formula V-C

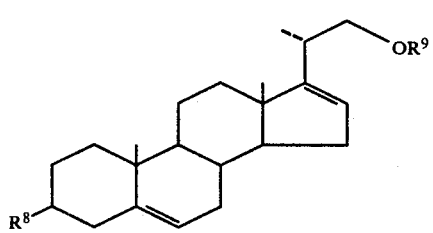

wherein $R^8$ is as above; and $R^9$ is acyl.

The reaction conditions, solvents and reagents for the formation of the compound of formula V-C are the same as those for the formation of the compound of formula II-B.

The compounds of formulas V-B or V-C are then treated with anhydrous pyridine and methanol to produce a compound of the formula

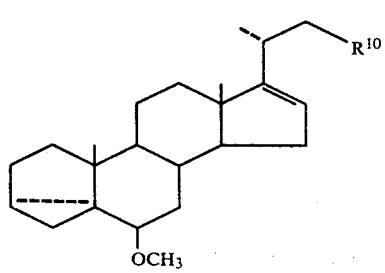

wherein $R^{10}$ is hydroxy, or a compound of the formula

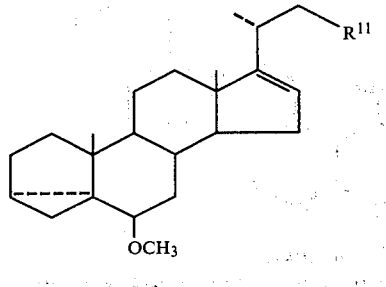

V-E wherein $R^{11}$ is acyloxy.

The compound of formula V-B will produce the compound V-D wherein $R^{10}$ is hydroxy, and the compound of formula V-C will produce the compound V-E wherein $R^{11}$ is acyloxy.

The foregoing reaction is carried out in the presence of a weak base such as anhydrous pyridine in the presence of methanol at reflux temperatures.

The compounds of formula V-D or V-E are then catalytically hydrogenated to produce the compounds of formula V-F

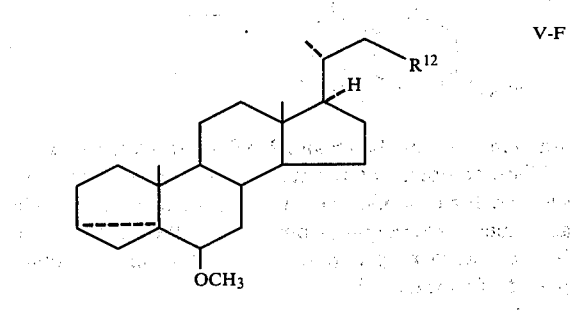

V-F wherein $R_{12}$ is hydroxy or acyloxy.

The reaction is carried out in a hydrogen atmosphere in the presence of a suitable hydrogenation catalyst such as platinum on charcoal, platinum oxide or Raney nickel as previously described.

The intermediates prepared by the process of the present invention have the natural steroid stereochemistry a the C-20 position and are suitable for the preparation of a number of different steroid compounds.

For example, 1α,25-dihydroxycholesterol may be prepared by reacting a compound of the formula

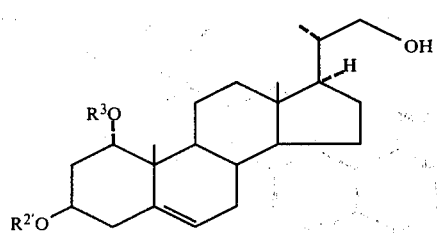

III-C wherein $R^3$ and $R^{2'}$ are both acyl, with paratoluenesulfonyl chloride in the presence of a weak base such as pyridine at temperatures ranging from $-10°$ to $40°$ C. to produce the compound of formula

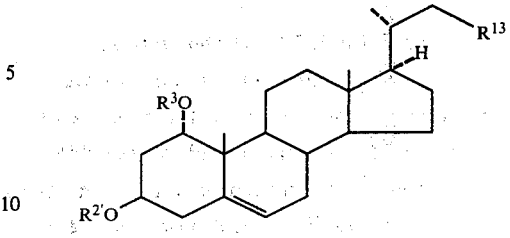

VI wherein $R^3$ and $R^{2'}$ are as above; and $R^{13}$ is p-toluenesulfonyloxy.

The compound of formula VI is in turn reacted with lithium aluminum hydride in the presence of an inert aprotic solvent such as tetrahydrofuran at temperatures ranging from $-20°$ to $0°$ C. so as to produce a compound of the formula

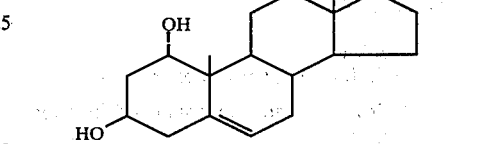

IX wherein $R^{13}$ is as above.

The compound of formula IX is in turn reacted with a conventional hydroxy protecting group such as 3,4-dihydro-2H-pyran and anhydrous p-toluenesulfonic acid at room temperature followed by treatment with sodium bicarbonate so as to produce the compound of formula VIII

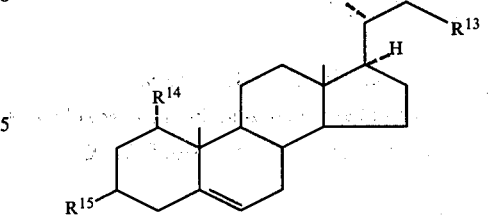

VIII wherein $R^{14}$ and $R^{15}$ are tetrahydropyranyloxy; and $R^{13}$ is as above.

The compound of formula VIII is in turn reacted with the lithium salt of 3-methyl-3-tetrahydropyranyloxybut-1-yne in hexane under an inert atmosphere at temperatures ranging from 20° to 150° C. to produce a compound of the formula

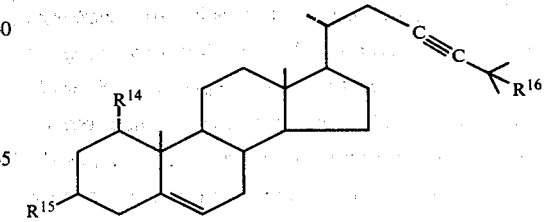

IX wherein $R^{14}$ and $R^{15}$ are as above; and $R^{16}$ is tetrahydropyranyloxy.

The compound of formula IX is treated with a hydrogenation catalyst such as Raney nickel under a hydrogen atmosphere at normal pressure in the presence of sodium bicarbonate to selectively reduce the triple bond, and the resulting tritetrahydropyranyl ether is treated with paratoluenesulfonic acid monohydrate in methanol to produce 1α,3β-25-trihydroxycholest-5-ene (1α,25-dihydroxycholesterol) of formula X.

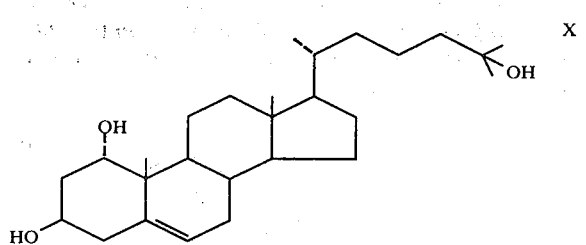

In an alternative embodiment for the preparation of 1α,25-dihydroxycholesterol, the compound of formula III-B

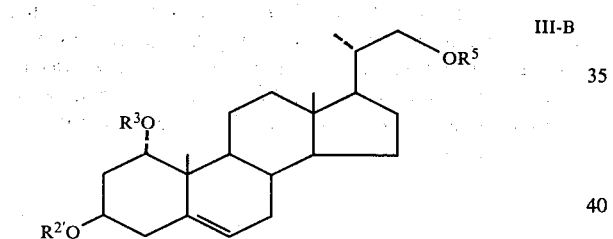

wherein $R^3$ and $R^{2'}$ are acyl; and $R^5$ is acyl,
is treated with strong base such as sodium hydroxide at reflux to produce the compound of formula III-C

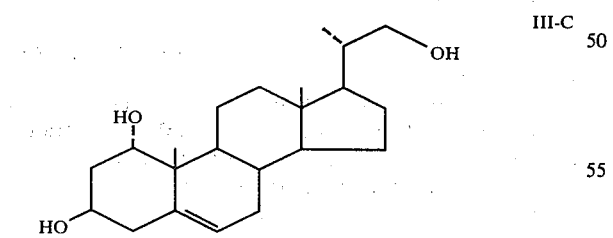

The compound of formula III-C is in turn reacted in a manner to selectively acylate the hydroxy group at the 21-position by reacting the compound of formula III-C with for example, acetic anhydride in the presence of lead diacetate-trihydrate in a weak base such as dimethylformamide at room temperature to produce a compound of the formula

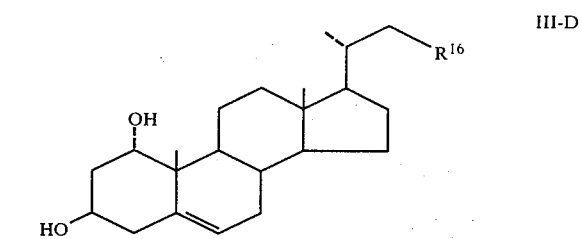

wherein $R^{16}$ is acyloxy.

The compound of formula III-D is reacted in the presence of a conventional hydroxy protecting group such as, for example, 3,4-dihydro-2H-pyran with anhydrous p-toluenesulfonic acid in benzene at temperatures ranging from −20° to 0° C. followed by treatment with sodium bicarbonate and extraction with ether to yield the compound of formula XI

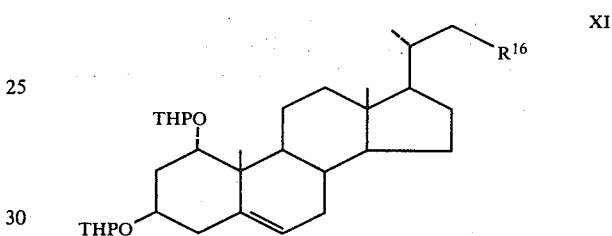

wherein $R^{16}$ is as above; and THP is tetrahydropyranyl.

The compound of formula XI is reacted with base such as, for example, methanolic potassium hydroxide at temperatures ranging from −20° to 100° C. to hydrolyze the acyloxy group $R^{16}$ so as to produce a compound of formula XII

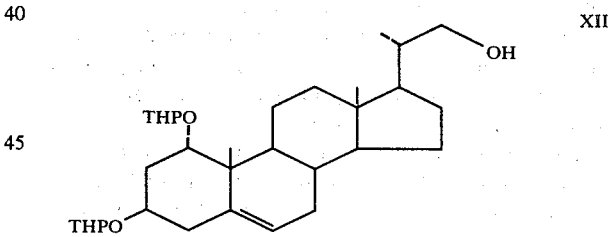

The compound of formula XII is transformed into a compound of formula XIII

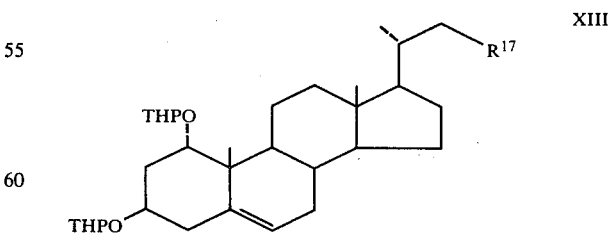

wherein $R^{17}$ is a conventional leaving group such as p-toluenesulfonyloxy,
by reaction with paratoluenesulfonyl chloride in the presence of a weak base such as pyridine at temperatures ranging from −10° to 40° C.

The compound of formula XIII is then reacted with the lithium salt of 3-methyl-3-tetrahydropyranyloxybut-1-yne in hexane under an inert atmosphere at temperatures ranging from 20° to 150° C. to produce a compound of the formula IX.

The compound of formula IX is in turn treated with a hydrogenation catalyst such as Raney nickel under a hydrogen atmosphere at normal pressure in the presence of sodium bicarbonate to selectively reduce the triple bond, and the resulting tritetrahydropyranyl ether is treated with paratoluenesulfonic acid monohydrate in methanol to produce $1\alpha,3\beta$-25-trihydroxycholest-5-ene ($1\alpha$,25-dihydroxycholesterol) of formula X.

25-hydroxycholesterol may be prepared from the compound of formula III, where $R^1$ is hydrogen and $R^2$ is acyloxy, by procedures described in the prior art in Y. Fujimoto et al., *J. Chem. Soc., Perkin I,* 1975, 2302 and R. R. Muccino et al., *Steroids,* 36, 645 (1978).

25-hydroxycholesterol may be prepared using the compound of formula VIII as the starting material according to the procedures of U.S. Pat. No. 3,822,254 (1974).

24R,25-dihydroxycholesterol may be prepared using the compound of formula V-F, a known material, according to the procedures of U.S. Pat. No. 4,038,272 (1977).

The following examples are illustrative of the present invention and its utility for the preparation of steroid compounds:

EXAMPLE 1

Preparation of
(Z)-$1\alpha,3\beta$-Diacetyloxypregna-5,17(20)-diene

To a stirred suspension of 9.12 g (30 mmol) of $1\alpha$-hydroxydehydroepiandrosterone and 25.1 g (60 mmol) of ethyltriphenylphosphonium iodide in 250 ml of tetrahydrofuran under a nitrogen atmosphere was added portionwise over ca. 5 min., 6.7 g (60 mmol) of potassium tert.-butoxide. The reaction temperature rose to 30°. After stirring at room temperature over night (16 hr.), the reaction was heated at reflux (oil bath) for 4.5 hr. to produce (Z)-$1\alpha,3\beta$-pregna-5,17(20)-diene-1,3-diol (Tlc: EtOAc, showed starting material was consumed). On cooling to 50°, 60 ml of pyridine and 30 ml of acetic anhydride were added, and the reaction solution left stirring over night (18 hr.) and then heated at reflux for 2 hr. Acetylation was still incomplete (Tlc: 4:1, hexane—ethyl acetate showed mono and diacetates). Consequently, 100 mg of 4-dimethylaminopyridine was added, and heating at reflux was continued for 5 hr. Then, the reaction solution was diluted with 250 ml of 80% aqueous methanol (v/v) and, after cooling to room temperature, was extracted with $3 \times 200$ ml of hexane. The organic phases were washed in a countercurrent manner with 250 ml of 80% aq. methanol (v/v) and evaporated under reduced pressure to give 12.0 g of crude product. Chromatography on 500 g of silica gel prepared in hexane, and elution with 200 ml fractions of 8:1, hexane—ethyl acetate afforded, in fractions 7–11, 6.8 g of impure product and, in fractions 12–17, 4.2 g of pure product. The combined fractions 7–11, on rechromatography, gave 6.2 g of pure product. Thus, a total of 10.4 g (87%) of pure $1\alpha,3\beta$-diacetyloxypregna-5,17(20)-diene as an amorphous solid, was obtained as a 95:5 mixture of Z and E isomers, respectively. An analytical sample of (Z)-$1\alpha,3\beta$-diacetyloxypregna-5,17(20)-diene, obtained by two recrystallizations from methanol, had mp 90°–91°.

EXAMPLE 2

Preparation of
(20S)-20-Methylpregna-5,16-diene-$1\alpha,3\beta,21$-triol 1,3-Diacetate To a stirred suspension of 4.0 g (10.0 mmol) (Z)-pregna-5,17(20)-diene-$1\alpha,3\beta$-diol diacetate and 0.90 g (30 mmol of monomer) of paraformaldehyde in 50 ml of methylene chloride under a nitrogen atmosphere was added 10 ml of a methylene chloride solution of boron trifluoride etherate (1:90, v/v). After 5 min., 100 ml of saturated aq. sodium bicarbonate was added, and the turbid two-phase mixture was passed through a glass fiber filter. The filtrate was extracted with $2 \times 50$ ml of methylene chloride. The organic phases were backwashed with 50 ml of saturated aq. sodium bicarbonate, dried ($Na_2SO_4$) and evaporated under reduced pressure to give 4.3 g of a solid foam which was applied to a column of 1 kg of silica gel prepared in hexane, washed with 1 L. of 8:1 hexane—ethyl acetate and then eluted with about 18 L. of 3:1 hexane—ethyl acetate on a fraction collector (20 ml cuts) to give 3.00 g of pure product (Tlc: silica gel, 1:1, EtOAc—hexane). By rechromatographing the combined impure fractions, an additional 0.46 g of product was obtained; thus, a total of 3.46 g (81%) of (20S)-20-methylpregna-5,16-diene-$1\alpha,3\beta,21$-triol 1,3-diacetate as an amorphous solid, was obtained. An analytical sample obtained by two crystallizations from hexane—ethyl acetate followed by recrystallization from methanol—water had mp 121°–122°.

EXAMPLE 3

Preparation of
(20S)-20-Methylpregn-5-ene-$1\alpha,3\beta,21$-triol 1,3-Diacetate To a solution of 860 mg (2.0 mmol) of (20S)-20-methylpregna-5,16-diene-$1\alpha,3\beta,21$-triol 1,3-diacetate in 50 ml of absolute ethanol was added 89 mg of 5% platinum on charcoal. The suspension was stirred under a hydrogen atmosphere at 23° until (2 hr.) the hydrogen uptake was 48 ml (theory 48.8 ml). The catalyst was removed by filtration (several filtrations were necessary to remove colloidal charcoal) through diatomaceous earth and was washed several times with methylene chloride. The filtrate was evaporated under reduced pressure, and the residue, 835 mg (97%), was recrystallized from 20 ml of hexane (cooled to $-5°$) to yield 746 mg (86%) of (20S)-20-methylpregn-5-ene-$1\alpha,3\beta,21$-triol 1,3-diacetate as white crystals, mp 133.5°–134.5°.

EXAMPLE 4

Preparation of
(20S)-20-Methylpregna-5,16-diene-$1\alpha,3\beta,21$-triol Triacetate To a stirred solution of 2.2 g (5.5 mmol) (Z)-pregna-5,17(20)-diene-$1\alpha,3\beta$-diol diacetate, 0.75 g (2.5 mmol of monomer) of paraformaldehyde and 5 ml (50 mmol) of acetic anhydride in 5 ml of methylene chloride uner an argon atmosphere was added 5 ml of a methylene chloride solution of boron trifluoride (1:90, v/v). After 2 hr., the bluish solution was poured into 500 ml of 5% sodium bicarbonate and allowed to stir overnight before extraction with $3 \times 100$ ml of ethyl acetate. The organic phases were washed with $3 \times 50$ ml of saturated sodium bicarbonate and 50 ml of brine in a counter-current manner. The combined organic phases were dried (Na$_2$SO$_4$), filtered and evaporated to give 3.0 g of residue. Chromatography on 500 g of silica gel prepared in and eluted with 5:1 hexane—ethyl acetate (20 ml fractions) gave, after combination of fractions according to tlc (2 developments in 2:1, hexane—EtOAc), 1.275 g in fractions 131–190 and 0.874 g in fractions 191–291. The latter fraction was rechromatographed on a Waters high pressure liquid chromatography instrument using 4:1 hexane—EtOAc to afford an additional 0.580 g. Thus, a total of 1.855 g (71%) of (20S)-20-methylpregna-5,16-diene-1α,3β,21-triol triacetate, mp 116°–118°, was obtained. An analytical sample obtained by recrystallization from methanol and then from acetonitrile had mp 119.5°–120.5°.

EXAMPLE 5

Preparation of (20S)-20-Methylpregna-5,16-diene-3β,21-diol Diacetate

To a stirred solution of 1.370 g (4.0 mmol) of (Z)-3β-acetoxypregna-5,17(20)-diene, 1.20 g (40 mmol) of paraformaldehyde and 8 ml (85 mmol) of acetic anhydride in 16 ml of methylene chloride under a nitrogen atmosphere was added 4 ml of boron trifluoride etherate solution in methylene chloride (1:90, v/v). Within one hour, the solution gradually became dark blue. After 5 hr., most of the methylene chloride was removed on a rotary evaporator (bath at room temperature), and the remaining solution was cautiously poured into 120 ml of cold saturated aqueous sodium bicarbonate and stirred over night before extraction with 2×60 ml of methylene chloride. The combined organic phases were filtered through a bed of diatomaceous earth (to remove suspended paraformaldehyde), dried (Na$_2$SO$_4$) and evaporated under reduced pressure to give 1.76 g of yellowish solid. Recrystallization from acetonitrile afforded 0.98 g (59%) of (20S)-20-methylpregna-5,16-diene-3β,21-diol diacetate as white crystals, mp 116°–117°. The analytical sample was recrystallized from acetonitrile: mp 117°–118°.

EXAMPLE 6

Preparation of (20S)-20-Methylpregn-5-ene-3β,21-diol Diacetate

A suspension of 414 mg (1 mmol) of (20S)-20-methylpregna-5,16-diene-3β,21-diol diacetate, 50 ml of 2B alcohol and 50 mg of 5% platinum on charcoal was stirred at 20° under an atmosphere of hydrogen until (1 hr.) an uptake of 22.3 ml (theoretical 24 ml) was observed; the catalyst was removed by filtration through a bed of diatomaceous earth and was washed several times. Evaporation of the filtrate afforded 413 mg of white solid, mp 121°–125°. Recrystallization from 3 ml of acetonitrile afforded 298 mg (71%) of (20S)-20-methylpregn-5-ene-3β,21-diol diacetate as white crystals, mp 125°–127° (reported mp 127°–129°).

EXAMPLE 7

Preparation of (20S)-20-Methylpregna-5,16-diene-3β,21-diol 3-Acetate (20S)-20-methylpregna-5,16-diene-3β,21-diol 3-acetate was prepared according to the following embodiments a. through x.:

a. To a stirred solution of 34.2 g (0.10 mol) of (Z)-pregna-5,17(20)-dien-3β-ol acetate and 9.0 g (0.30 mol of monomer) of paraformaldehyde in 500 ml of methylene chloride under a nitrogen atmosphere was added 91 ml of a solution of boron trifluoride etherate in methylene chloride (1:90, v/v). After 10 min., 1000 ml of saturated sodium bicarbonate was added all at once, and the suspension was filtered. The methylene chloride phase of the filtrate was separated, dried (Na$_2$SO$_4$) and evaporated to give 27.1 g of solid residue. Chromatography on 1.5 kg of silica gel prepared in and eluted with hexane—ethyl acetate (4:1) afforded (fractions combined according to tlc: hexane—EtOAc, 4:1) 31.2 g (84%) of (20S)-20-methylpregna-5,16-diene-3β,21-diol 3-acetate as a white solid, mp 170°–171°. An analytical sample, crystallized from ethyl acetate, had mp 168°–170°.

b. Boron trifluoride hydrate was used as the catalyst to prepare (20S)-20-methylpregna-5,16-diene-3β,21-diol 3-acetate in a procedure similar to embodiment "a".

c. Boron trifluoride methanol complex was used as the catalyst to prepare (20S)-20-methylpregna-5,16-diene-3β,21-diol 3-acetate in a procedure similar to embodiment "a".

d. Boron trifluoride ethylamine complex was used as the catalyst to prepare (20S)-20-methylpregna-5,16-diene-3β,21-diol 3-acetate in a procedure similar to embodiment "a".

e. Aluminum chloride was used as the catalyst to produce (20S)-20-methylpregna-5,16-diene-3β,21-diol 3-acetate in a procedure similar to embodiment "a".

f. Aluminum chloride was used as the catalyst and benzene as the solvent to produce (20S)-20-methylpregna-5,16-diene-3β,21-diol 3-acetate in a procedure similar to embodiment "a".

g. Zinc chloride was used as the catalyst to produce (20S)-20-methylpregna-5,16-diene-3β,21-diol 3-acetate in a procedure similar to embodiment "a".

h. Stannic chloride was used as the catalyst to produce (20S)-20-methylpregna-5,16-diene-3β,21-diol 3-acetate in a procedure similar to embodiment "a".

i. Boron trichloride was used as the catalyst to produce (20S)-20-methylpregna-5,16-diene-3β,21-diol 3-acetate in a procedure similar to embodiment "a".

j. Titanium tetrachloride was used as the catalyst to produce (20S)-20-methylpregna-5,16-diene-3β,21-diol 3-acetate in a procedure similar to embodiment "a".

k. Methanesulfonic acid was used as the catalyst to produce (20S)-20-methylpregna-5,16-diene-3β,21-diol 3-acetate in a procedure similar to embodiment "a".

l. Para-toluenesulfonic acid monohydrate was used as the catalyst to produce (20S)-20-methylpregna-5,16-diene-3β,21-diol 3-acetate in a procedure similar to embodiment "a".

m. Trifluoroacetic acid was used as the catalyst to produce (20S)-20-methylpregna-5,16-diene-3β,21-diol 3-acetate in a procedure simlar to embodiment "a".

n. Oxalic acid monohydrate was used as the catalyst to produce (20S)-20-methylpregna-5,16-diene-3β,21-diol 3-acetate in a procedure similar to embodiment "a".

o. Chloroform was used as the solvent to produce (20S)-20-methylpregna-5,16-diene-3β,21-diol 3-acetate in a procedure similar to embodiment "a".

p. Carbon tetrachloride was used as the solvent to produce (20S)-20-methylpregna-5,16-diene-3β,21-diol 3-acetate in a procedure similar to embodiment "a".

q. Toluene was used as the solvent to produce (20S)-20-methylpregna-5,16-diene-3β,21-diol 3-acetate in a procedure similar to embodiment "a".
r. Tetrahydrofuran was used as the solvent to produce (20S)-20-methylpregna-5,16-diene-3β,21-diol 3-acetate in a procedure similar to embodiment "a".
s. Diethyl ether was used as the solvent to produce (20S)-20-methylpregna-5,16-diene-3β,21-diol 3-acetate in a procedure similar to embodiment "a".
t. Acetic acid was used as the solvent to produce (20S)-20-methylpregna-5,16-diene-3β,21-diol 3-acetate in a procedure similar to embodiment "a".
u. Methanesulfonic acid was used as the catalyst and formalin (aq. formaldehyde) was substituted for paraformaldehyde to produce (20S)-20-methylpregna-5,16-diene-3β,21-diol 3-acetate in a procedure similar to embodiment "a".
v. p-Toluenesulfonic acid monohydrate was used as the catalyst and formalin was substituted for the paraformaldehyde to produce (20S)-20-methylpregna-5,16-diene-3β,21-diol 3-acetate in a procedure similar to embodiment "a".
w. Sulfuric acid was used as the catalyst and formalin was substituted for the paraformaldehyde to produce (20S)-20-methylpregna-5,16-diene-3β,21-diol 3-acetate in a procedure similar to embodiment "a".

EXAMPLE 8

Preparation of (20S)-20-Methylpregna-5,16-diene-3β,21-diol

To a stirred suspension of 601 mg (2 mmol) of (Z)-pregna-5,17(20)-dien-3β-ol, 180 mg (3 mmol of monomer) of paraformaldehyde and 10 ml of methylene chloride under a nitrogen atmosphere was added 2 ml of boron trifluoride etherate in methylene chloride (1:90, v/v). After 6 min., 25 ml of saturated sodium bicarbonate was added. The suspension was extracted with 2×20 ml of methylene chloride which were washed with 25 ml of brine. The combined organic phases were dried (Na₂SO₂) and evaporated. The residue contained considerable unreacted starting material (tlc: hexane—EtOAc, 1:1), so it was recycled as above for 10 min. (reaction time) to give 694 mg of off-white solid after workup. Chromatography on silica gel and elution with methylene chloride—ethyl acetate (5:1) afforded, after combination of fractions according to tlc (hexane—EtOAc, 1:1), a total of 406 mg (61%) of (20S)-20-methylpregna-5,16-diene-3β,21-diol, mp 190°–192.5° (vac.).

EXAMPLE 9

Preparation of (20S)-20-Methylpregna-5,16-diene-3β,21-diol

A solution of 1.2 g (2.9 mmol) of (20S)-20-methylpregna-5,16-diene-3β, 21-diol diacetate and 0.16 g of sodium hydroxide in 25 ml of methanol was heated at reflux for 1 hr. and then poured into 250 ml of water. The resulting suspension was extracted with 3×100 ml of ethyl acetate which were washed in a counter-current manner with 100 ml of brine, dried (Na₂SO₄) and evaporated to give 0.95 g of white solid. Recrystallization from ethyl acetate afforded, in 2 crops, 0.86 (90%) of (20S)-20-methylpregna-5,16-diene-3β,21-diol as white crystals, mp 182°–187°. An analytical sample crystallized from ethyl acetate: mp 183°–184°, mp 193.5°–194.5° (vac).

EXAMPLE 10

Preparation of (Z)-Pregna-5,17(20)-dien-3β-ol-p-Toluenesulfonate

To a solution of 1.80 g (6.0 mmol) (Z)-pregna-5,17(20)-dien-3β-ol in 8 ml of pyridine under a nitrogen atmosphere was added 1.26 g (6.6 mmol) of p-toluenesulfonyl chloride. Precipitation (pyridinium hydrochloride) began after 3 hr. After 19 hr., an additional 1.03 g (5.4 mmol) of p-toluenesulfonyl chloride was added. The reaction was left stirring for 5 days and then was poured into a stirred solution of 150 ml of 5% aqueous sodium bicarbonate cooled to 7°. After 30 min., the precipitate was removed by filtration, the filter cake washed with 2×15 ml of water and then dried over night to a vacuum dessicator (Drierite) at about 1 mm Hg to afford 2.50 g (92%) of crude product suitable for the next step. (Unstable to chromatography). An analytical sample was recrystallized from hexane to give (Z)-pregna-5,17(20)-dien-3β-ol-p-toluenesulfonate as white crystals, mp 119°–119.3°.

EXAMPLE 11

Preparation of (20S)-20-Methylpregna-5,16-diene-3,21-diol 21-Acetate 3-p-Toluenesulfonate To a stirred solution of 11.3 g (25 mmol) of (Z)-pregna-5,17(20)-dien-3β-ol p-toluenesulfonate, 7.51 g (0.25 mol) of paraformaldehyde and 50 ml (0.53 mol) of acetic anhydride in 100 ml of methylene chloride was added 25 ml of a methylene chloride solution of boron trifluoride etherate (1:90, v/v). After 5.5 hr. at room temperature, the turbid bluish solution was passed through a glass fiber filter and to the filtrate was added, with stirring, 1000 ml of saturated aqueous sodium bicarbonate. Stirring was continued for 45 min., and then the suspension was extracted with 3×250 ml of methylene chloride. The organic phases were washed with 100 ml of water in a counter-current manner, dried (Na₂SO₄) and evaporated under reduced pressure to give 14.5 g of crude product which could be used directly in the next step (unstable to chromatography). An analytical sample was recrystallized from hexane to afford (20S)-20-methylpregna-5,16-diene-3,21-diol 21-acetate 3-p-toluenesulfonate as white needles, mp 109°–110°.

EXAMPLE 12

Preparation of (20S)-3β,5α,6β-Methoxy-20-methyl-3,5-cyclopregn-16-en-21-ol Acetate A solution of 11.0 g (19 mmol) of (20S)-20-methylpregna-5,16-diene-3,21-diol 21-acetate 3-p-toluenesulfonate, 4.6 ml of anhydrous pyridine and 70 ml of methanol was heated at reflux for 3 hr. and then was evaporated under reduced pressure. About 50 ml of toluene was added and evaporated under reduced pressure. The residue was triturated with 50 ml of hexane and filtered. The filter cake (pyridinium p-toluenesulfonate) was washed with 3×50 ml of hexane. The filtrate was evaporated under reduced pressure and the residue applied to column of 200 g of silica gel in hexane. Elution with 4:1 hexane—ethyl acetate afforded 7.61 g of crude product. High pressure liquid chromatography using 10:1 hexane—ethyl acetate yielded a total of 4.84 g (66%) of amorphous (20S)-3β,5α,6β-methoxy-20-methyl-3,5-cyclopregn-16-en-21-ol acetate.

EXAMPLE 13

Preparation of
(20S)-3β,5α,6β-Methoxy-20-methyl-3,5-cyclopregnan-21-ol Acetate

A suspension of 380 mg (1.0 mmol) of (20S)-3β,5α,6β-methoxy-20-methyl-3,5-cyclopregn-16-en-21-ol acetate, 100 mg (1.2 mmol) of sodium bicarbonate, 50 mg of 5% platinum on charcoal and 25 ml of absolute ethanol was stirred under a hydrogen atmosphere for 23 hrs. (uptake was 20 ml: theory, 24 ml). The catalyst was removed by filtration through a diatomaceous earth pad and was washed with 2×15 ml of ethanol. The filtrate was evaporated, and, after, the addition of 20 ml of water was extracted with 2×20 ml of methylene chloride. The organic phases were backwashed in a countercurrent manner with 10 ml of water, dried (Na₂SO₄) and evaporated to give 352 mg (90%) of (20S)-3β,5α,6β-methoxy-20-methyl-3,5-cyclopregnan-21-ol acetate as a white solid, mp 116°–123°. Shown to be identical to an authentic sample by TLC and NMR.

EXAMPLE 14

Preparation of
(20S)-1α,3β-Diacetyloxy-20-methyl-21-p-toluenesulfonyloxypregn-5-ene In a 250 ml 4-neck flask equipped with a stirrer, 50-ml dropping funnel with pressure equalizer, thermometer and drying tube moisture barrier, a solution of 20.0 g (0.046 mol) of (20S)-20-methylpregn-5-ene-3β,21-diol diacetate in 100 ml pyridine was cooled to approximately 0°, and, while being stirred, a solution of 11.2 g (0.058 mol) of p-toluenesulfonyl chloride in 40 ml pyridine was dripped (15 min.) into the flask in such a way that the temperature did not rise above 3°. The reaction mixture was stirred for a further 5 hr. in an ice bath and poured over 300 g ice. By the addition of approximately 100 ml of 25% hydrochloric acid the mixture was brought up to pH=5 (pH-meter), extracted first with 300 ml and then twice with 200 ml (i.e., a total of 700 ml) of ether. The ether extracts were washed successively with 300 ml of sat. NaHCO₃ solution and twice with 150 ml (i.e., total of 300 ml) of sat. NaCl solution, combined, dried over sodium sulfate and concentrated under vacuum at 40°. The residue was dissolved in 200 ml of benzene and concentrated at 40° under vacuum. The resulting residue was treated twice more in a similar way, for which a total of 400 ml benzene was required. The residue, 26.5 g, continued (20S)-1α,3β-diacetyloxy-20-methyl-21-p-toluenesulfonyloxypregn-5-ene.

EXAMPLE 15

Preparation of
(20S)-1α,3β-Dihydroxy-20-methyl-21-p-toluenesulfonyloxypregn-5-ene In a 2.5 l 4-neck flask equipped with a stirrer, 500 ml dropping funnel with pressure equilizer, thermometer and argon inlet, 800 ml of tetrahydrofuran (product from freshly-opened bottle was stored for 16 hr. over molecular sieves) at room temperature was added in one portion with stirring to 10.84 g (0.28 mol) of lithium aluminum hydride. The suspension was cooled to −20°, and, during cooling and stirring for 30 min., a solution of 26.5 g crude (20S)-1α,3β-diacetyloxy-20-methyl-21-p-toluenesulfonyloxypregn-5-ene in 450 ml tetrahydrofuran under an argon atmosphere was dripped into the flask in such a way that the temperature did not surpass −18°. After stirring for 1.5 hr. under argon at −20°, 1.2 l of tetrahydrofuran—ethyl acetate (1:1) was added to the suspension over a period of 30 min. in such a way that the temperature did not surpass −18°. The cold reaction mixture was poured into a stirred solution, precooled to 0°, of 0.8 l of 2 M potassium sodium tartrate solution. The organic solvent was removed under vacuum at 40°, and the aqueous residue was extracted first with 500 ml and then twice with 300 ml (total of 1.1 l) of ether. The ether extracts were washed successively 2 times with 250 ml of water and 2 times with 250 ml of sat. NaCl solution, combined and dried over sodium sulfate. After removal of the solvent under reduced pressure at 40°, the residue amounted to 24.1 g of crude (20S)-1α,3β-dihydroxy-20-methyl-21-p-toluenesulfonyloxypregn-5-ene (the crude product still contained some unreacted triol because of incomplete tosylation).

EXAMPLE 16

Preparation of
(20S)-1α,3β-Bis[(tetrahydro-2H-pyran-2-yl)oxy]-20-methyl-21-p-toluenesulfonyloxypregn-5-ene A solution of 24.1 g of (20S)-1α,3β-dihydroxy-20-methyl-21-p-toluenesulfonyloxypregn-5-ene in 1.11 l of benzene was concentrated at 40° under vacuum to approximately 500 ml. The concentrate was added to 8.27 g or 9.0 ml (0.097 mol) of 3,4-dihydro-2H-pyran and 0.18 g (1.04 mol) of anhydrous p-toluenesulfonic acid and stored well sealed for 1.5 hr. at room temperature. The mixture was poured onto 500 ml of sat. NaHCO₃ solution, 200 ml of ether was added, and, after shaking, the organic phase was separated. The aqueous layer was washed twice with 300 ml (total of 600 ml) of ether. The 3 organic extracts were successively washed twice with 250 ml (total of 500 ml) of sat. NaCl solution, combined and dried over sodium sulfate. The residue remaining after concentrating at 40° under vacuum was dissoled in 30 ml of ether and added to a column prepared with hexane—ether (9:1) and 1 kg of silica gel. Elution with hexane—ether mixtures (4:1) yielded 17.2 g (56%) of (20S)-1α,3β-bis[(tetrahydro-2H-pyran-2-yl)oxy]-20-methyl-21-p-toluenesulfonyloxypregn-5-ene as a yellow gum.

EXAMPLE 17

Preparation of
1α,3β,25-Tris[(tetrahydro-2H-pyran-2-yl)oxy]-cholest-5-en-23-yne

In a 1.5 l 4-neck flask equipped with stirrer, 100 ml dropping funnel with pressure equalizer, 30-cm Dimroth condenser, thermometer and argon-supply, a solution of 16.85 g (0.1 mol) of 3-methyl-3[(tetrahydro-2H-pyran-2-yl)oxy]-but-1-yne (prepared from 3-hydroxy-3-methylbut-1-yne and 3,4-dihydro-2H-pyran) in 300 ml of dioxane with constant stirring and under argon for 30 min. at 9°, was added drop by drop 50 ml (approximately 0.1 ml) of approximately 2 M n-butyl lithium in hexane. The solution was stirred for 2 hr. at 9° and for a further 2 hr. at room temperature. To the light yellow mixture was then added, in one portion, a solution of 22.4 g of crude (20S)-1α,3β-bis[(tetrahydro-2H-pyran-2-yl)oxy]-20-methyl-21-p-toluenesulfonyloxypregn-5-ene (corresponding to approximately 0.033 mol), in 40 ml of dioxane and stirred for 64 hr. at 105° under argon. The mixture, which became dark yellow and cloudy, was cooled to room temperature, poured onto 500 g of ice, and the emulsion was extracted 3 times with 200 ml of ether. The ether extracts were washed successively 2 times with 200 ml of water, combined, dried over sodium sulfate and concentrated under vacuum at 40°. The residue was dissolved in 200 ml of toluene and concentrated under vacuum at 40°. The residue was treated twice more in the same way to remove dioxane and excess 3-methyl-3[(tetrahydro-2H-pyran-2-yl)oxy]-but-1-yne). After drying for 1 hr. under vacuum at room temperature, the remaining light brown oil, 34.1 g (which contained some 3-methyl-3[(tetrahydro-2H-pyran-2-yl)oxy]-but-1-yne and ditetrahydropyranyloxytosylate), was dissolved in ether and added to a column prepared with hexane—ether (9:1), containing 4 ml of pyridine/1, and 1 kg of silica gel. Elution with hexane—ether (4:1) mixtures (without the addition of pyridine) yielded 19.6 g (88%) of 1α,3β,25-tris[(tetrahydro-2H-pyran-2-yl)oxy]-cholest-5-en-23-yne.

EXAMPLE 18

Preparation of
1α,3β,25-Tris[(tetrahydro-2H-pyran-2-yl)oxy]-cholest-5-ene

A suspension of 14 ml of Raney nickel (water was decanted off from the commercial aqueous suspension; the residue was mixed with ethanol, and, after being allowed to settle approximately 15 min., the supernatant liquid was removed. This washing procedure with ethanol was repeated 4 more times) in 200 ml of ethanol was shaken overnight at room temperature under a hydrogen atmosphere (consumption of hydrogen 180 ml). After the addition of 2.0 g of sodium bicarbonate and 6.7 g of 1α,3β,25-tris[(tetrahydro-2H-pyran-2-yl)oxy]-cholest-5-en-23-yne, the mixture was shaken for 24 hr. at room temperature under a hydrogen atmosphere whereby 460 ml of hydrogen was absorbed. After this period, no further hydrogen absorbtion was observed. The mixture was filtered over diatomaceous earth, the cake was washed with a total of 500 ml of ethanol, and the combined filtrates were concentrated under vacuum at 40°. The residue was 6.7 g of pale yellow resin containing 1α,3β,25-tris[(tetrahydro-2H-pyran-2-yl)oxy]-cholest-5-ene.

EXAMPLE 19

Preparation of
1α,3β,25-Trihydroxy-cholest-5-ene(1α,25-dihydroxy-cholesterol)

A mixture of 6.7 g 1α,3β,25-tris[(tetrahydro-2H-pyran-2-yl)oxy]-cholest-5-ene and 70 ml of methanol was mixed with 0.5 g of p-toluenesulfonic acid monohydrate and stirred for 4 hr. at room temperature. After stirring for 20 min., the solution became clear. During continuous stirring for approximately 30 min., 150 ml of water was dripped into the solution. The crystalline product precipitated was filtered, washed with water and dried at room temperature for 24 hr. under vacuum over NaOH pellets and then for a further 16 hr. under high vacuum to afford 4.15 g of 1α,25-dihydroxycholesterol, mp 173°–175°, of 90.7% purity. By direct GC comparison, it was determined that an impurity (1.8%) present in the product was 1α,3β,25-trihydroxy-5α-cholestane.

EXAMPLE 20

Preparation of
(20S)-20-Methylpregn-5-ene-1α,3β,21-triol

A solution of (20S)-20-methyl-1α,3β,21-triacetyloxypregn-5-ene in methanol was treated with sodium hydroxide at reflux to produce (20S)-20-methylpregn-5-ene-1α,3β,21-triol.

EXAMPLE 21

Preparation of
(20S)-21-Acetyloxy-20-methylpregn-5-ene-1α,3β-diol

To a solution of 2.4 g of lead diacetate-trihydrate in 180 ml of dimethylformamide and 24 ml of acetic anhydride was added 4.6 g of (20S)-20-methylpregn-5-ene-1α,3β,21-triol. After standing at room temperature for 24 hr., the mixture was poured onto 1 kg of a 3:1 water—ice mixture and then extracted with ether. The ether extract was washed with water, dried (Na₂SO₄) and evaporated by means of a water aspirator. The residue was chromatographed on 100 g of silica gel. Elution with 1:1 hexane—ether afforded 1.14 g (20%) of (20S)-3β,21-diacetyloxy-20-methylpregn-5-en-1α-ol, mp 148°–149°. Elution with ether gave first 0.24 g (4.6%) of (20S)-3β-acetyloxy-20-methylpregn-5-ene-1α,21-diol, mp 202°–203° and then 2.94 g (57%) of (20S)-21-acetyloxy-20-methylpregn-5-ene-1α,3β-diol, mp 121°–121°. Finally, elution with ethyl acetate afforded 0.79 g (17%) of starting triol.

EXAMPLE 22

Preparation of
(20S)-21-Acetyloxy-1α,3β-bis[(tetrahydro-2H-pyran-2-yl)oxy]-20-Methylpregn-5-ene To a solution of 2.7 g of (20S)-21-acetyloxy-20-methylpregn-5-ene-1α,3β-diol in 120 ml of benzene containing 30 mg of anhydrous p-toluenesulfonic acid was added 4.2 ml of 3,4-dihydro-2H-pyran. The reaction mixture was left at 20° for 2 hr. and then poured onto an ice-cold 5% sodium bicarbonate solution. The product was extracted with ether. The ether extract was washed with saturated sodium chloride solution, dried (Na₂SO₄) and evaporated under reduced pressure. After drying at 0.05 mm, 4.3 g of (20S)-21-acetoxy-1α,3β-bis[(tetrahydro-2H-pyran-2-yl)oxy]-20-methylpregn-5-ene was obtained which, after recrystallization from methanol—ether, had mp 155°–161°.

EXAMPLE 23

Preparation of
(20)S-1α,3β-Bis[(tetrahydro-2H-pyran-2-yl)oxy]-20-methylpregn-5-en-21-ol To a solution of 4.3 g of (20S)-21-acetyloxy-1α,3β-bis[(tetrahydro-2H-pyran-2-yl)oxy]-20-methylpregn-5-ene in 30 ml of methanol was added 16 ml of 10% methanolic potassium hydroxide. After being stirred at 20° for 16 hr., the solution was concentrated under reduced pressure (aspirator). Water was added to the residue, and the product extracted with benzene, dried (Na₂SO₄), evaporated under reduced pressure and dried at 30°/0.05 mm resulting in 3.7 g of (20S)-1α,3β-bis[(tetrahydro-2H-pyran-2-yl)oxy]-20-methylpregn-5-en-21-ol as an amorphous solid, mp 50°–67°.

EXAMPLE 24

Preparation of
(20S)-1α,3β-Bis[(tetrahydro-2H-pyran-2-yl)oxy]-20-methyl-21-(p-toluenesulfonyloxy)pregn-5-ene To a stirred solution of 3.7 g of (20S)-1α,3β-bis[(tetrahydro-2H-pyran-2-yl)oxy]-20-methylpregn-5-en-21-ol in 5 ml of pyridine at 0° was added a solution of 1.77 g of p-toluenesulfonyl chloride in 3 ml of pyridine dropwise over 10 min. After 165 min. at 0°, the mixture was poured into ice water and extracted with ether. The ether extract was washed with water, dried ($Na_2SO_4$) and evaporated under reduced pressure. The residue was dissolved in 100 ml of toluene, concentrated in a 50° bath at 11 mm and applied to 80 g of silica gel containing 1% pyridine. Elution with hexane—ether, 7:3, afforded 3.49 g (73%) of (20S)-1α,3β-bis[(tetrahydro-2H-pyran-2-yl)oxy]-20-methyl-21-(p-toluenesulfonyloxy)-pregn-5-ene as a white amorphous solid.

EXAMPLE 25

Preparation of
(Z)-1α,3β-Pregnene-5,17(20)-diene-1,3-diol
1,3-Bistrifluoroacetate A solution of (Z)-1α,3β-pregnene-5,17(20)-diene-1,3-diol, 10.0 g (31.6 mmol) in 100 ml of pyridine, was stirred under an argon atmosphere and cooled in an ice-bath. To this was added 12.5 ml (88.1 mmol) of trifluoroacetic anhydride, and the cold mixture was stirred for 1 hr. and then diluted with 250 ml of ethyl acetate. The organic phase was washed, until slightly acidic to pH paper, with a total of 450 ml of cold hydrochloric acid. Washing was continued with 2 150 ml portions equal to a total of 300 ml of water/sat. sodium chloride (1:1), along with 10 ml of methanol (to aid in separation), followed by 100 ml of water/sat. sodium bicarbonate (10:1) and 150 ml of water. After drying ($Na_2SO_4$), the solvent was removed in vacuo (55°) and crude (Z)-1α,3β-pregnene-5,17(20)-diene 1,3-bistrifluoroacetate was obtained. Yield: 15.48 g as a yellow oil.

EXAMPLE 26

Preparation of
(20S)-20-Methyl-1α,3β-ditrifluoroacetyloxpregna-5,16-diene-21-ol

1α,2β-ditrifluoroacetyloxy-23,24-bisnorchol-5,16-dien-22-ol, 15.48 g (30. 4 mmol), was dissolved in 155 ml of methylene chloride. To this was added 0.96 g (1.05 equiv.) of paraformaldehyde and 31 ml of a solution of boron trifluoride etherate in methylene chloride. The solution was allowed to stir at room temperature under an argon atmosphere for 65 min. while monitoring the reaction by TLC. The organic phase was washed with 80 ml of water/sat. sodium bicarbonate (75:5), 75 ml of water, 75 ml of sat. sodium chloride solution and dried ($Na_2SO_4$). Removal of the solvent in vacuo (55°) gave 15.81 g of (20S)-20-methyl-1α,3β-ditrifluoroacetyloxy-pregna-5,16-dien-21-ol as a brownish foam.

EXAMPLE 27

Preparation of
(20S)-1α,3β-Diacetyloxy-20-methylpregn-5-en-21-ol

A solution of (20S)-20-methyl-1α,3β-ditrifluoroacetyloxypregna-5,16-dien-21-ol (15.81 g) in 50 ml of ethyl acetate was treated with 1.0 g of charcoal at room temperature for 10 min. After filtration (diatomaceous earth), the solution was diluted with 170 ml of ethyl acetate, 1.63 g of 5% Pt/C was added, hydrogenation was carried out at room temperature (ca. 20° C.) and, essentially, atmospheric pressure. Hydrogen uptake was ca. 85% after 6 hr. However, the reaction was allowed to poceed over night (22 hr.) for convenience. Total $H_2$ uptake 741 ml (theory: 706 ml). The catalyst was removed by filtration over diatomaceous earth (transfer was completed with ethyl acetate). The solvent was removed (vacuo) at 55° to yield 15.42 g of (20S)-1α,3β-diacetyloxy-20-methylpregn-5-en-21-ol as a white foam.

EXAMPLE 28

Preparation of
(20S)-20-Methyl-1α,3β-ditrifluoroacetyloxypregn-5-en-21-ol p-Toluenesulfonate The hydrogenation product (20S)-1α,3β-diacetyloxy-20-methylpregn-5-en-21-ol, 15.42 g (28.5 mmol), was dissolved in 70 ml of pyridine, cooled and stirred in an ice-bath under an argon atmosphere and treated with 8.51 g (44.6 mmol) of p-toluenesulfonyl chloride. After 5.5 hr. in the cooling bath, 150 ml of ice and water was added and the product extracted with one 150 ml and two 75 ml equal to a total of 300 ml of ethyl acetate. The organic extract was washed with 300 ml total of 2 N hydrochloric acid (until slightly acid to pH paper), 60 ml of water, 30 ml of sat. sodium bicarbonate solution, 60 ml of water and 60 ml of sat. sodium chloride solution. After drying ($Na_2SO_4$) and removing the solvent in vacuo (40°), 18.03 g of product (20S)-20-methyl-1α,3β-ditrifluoroacetyloxypregn-5-en-21-ol p-toluenesulfonate was obtained as a white foam.

EXAMPLE 29

Preparation of
(20S)-20-Methyl-21-(p-toluenesulfonyloxy)pregn-5-ene-1α,3β-diol

Substance (20S)-20-methyl-1α,3β-trifluoroacetyloxy-pregn-5-en-21-ol p-toluenesulfonate, 18.03 g (25.9 mmol), was dissolved in 150 ml of methanol and cooled in a cold water bath while stirring under an argon atmosphere. To this was added (over 10 min.) 20 ml of a 20% potassium carbonate solution. The bath was removed, and the reaction was allowed to proceed at room temperature for 2.5 hr. TLC analysis showed incomplete reaction. Methanol, 100 ml, was added followed by 10 ml of a 40% potassium carbonate solution. After 1 hr., TLC analysis showed complete reaction. The product was caused to crystallize by the slow addition of 100 ml of water followed by chilling for 1 hr. in an ice-bath. The substance was collected and washed thoroughly on the filter with cold methanol—water (250:130) and then dried in vacuo (oven temperature 40° increased to 50°) to constant weight to yield 10.05 g (63.3%) of (20S)-20-methyl-21-(p-toluenesulfonyloxy)pregn-5-ene-1α,3β-diol as an off-white powder, mp 91°–99° (sintering).

What is claimed is:

1. A process for the synthesis of compounds of the formula

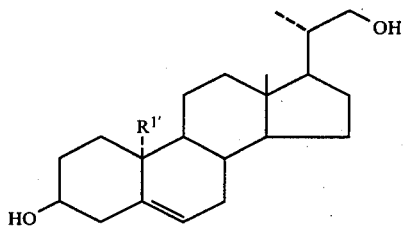

wherein R¹' is hydrogen or hydroxy,
which process comprises the steps of
a. reacting a compound of the formula

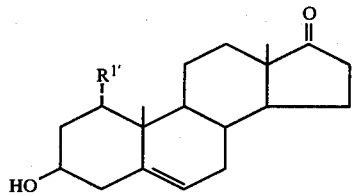

wherein R¹' is hydrogen or hydroxy,
with an ethyltriphenylphosphonium halide in the presence of strong base to yield a compound of the formula

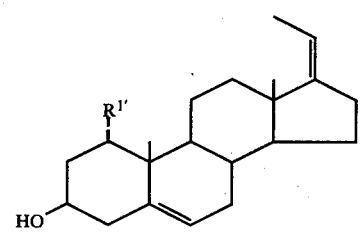

wherein R¹' is hydrogen or hydroxy;
b. reacting the reaction product of step a. with formaldehyde or a compound capable of generating formaldehyde in situ in an inert solvent at temperatures ranging from −20° to 45° C. in the presence of Lewis or protic acids to yield a compound of the formula

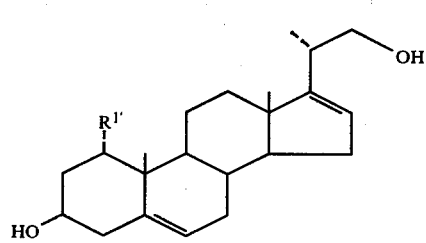

wherein R¹' is hydrogen or hydroxy;
c. reacting the reaction product of step b. with hydrogen in an inert solvent in the presence of a hydrogenation catalyst at temperatures ranging from 0° to 48° C. to yield a compound of formula

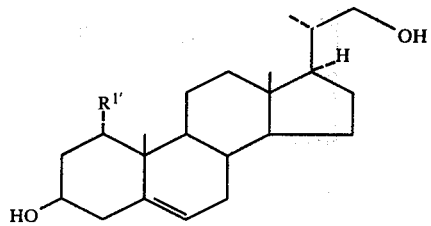

wherein R¹' is hydrogen or hydroxy.

2. A process for the synthesis of compounds of the formula

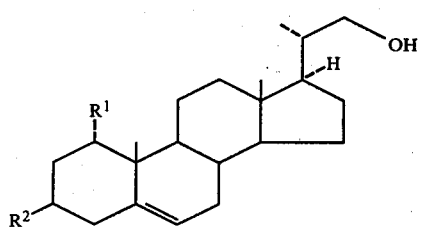

wherein R¹ is hydrogen, hydroxy or acyloxy; and R² is hydroxy or acyloxy,
which comprises the steps of
a. reacting a compound of the formula

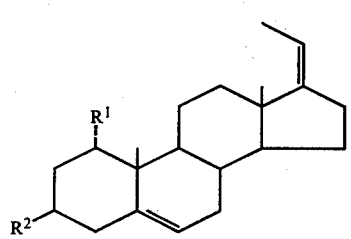

wherein R¹ is hydrogen, hydroxy or acyloxy; and R² is hydroxy or acyloxy, with formaldehyde or a compound capable of generating formaldehyde in situ in an inert solvent at temperatures ranging from −20° to 45° C. in the presence of Lewis or protic acids to yield compounds of the formula

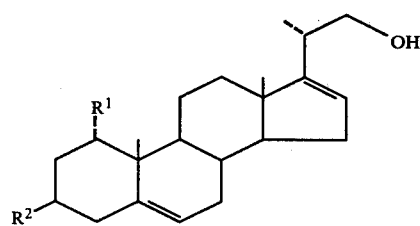

wherein R¹ is hydrogen, hydroxy or acyloxy; and R² is hydroxy or acyloxy;
b. reacting the reaction product from step a. with hydrogen in an inert solvent in the presence of a hydrogenation catalyst at temperatures ranging from 0° to 40° C. to yield compounds of the formula

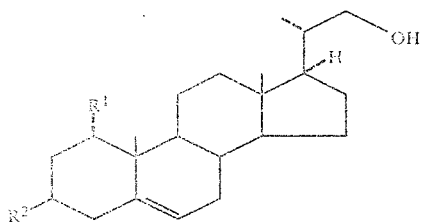

wherein $R^1$ is hydrogen, hydroxy or acyloxy; and $R^2$ is hydroxy or acyloxy.

3. The process according to claim 2 wherein said Lewis or protic acid is selected from the group consisting of boron trifluoride etherate, aluminum chloride, methanesulfonic acid and trifluoroacetic acid.

4. The process according to claim 3 wherein said Lewis acid is boron trifluoride etherate.

5. The process according to claim 4 wherein said formaldehyde-producing compound is paraformaldehyde.

6. The process according to claim 5 wherein said hydrogenation catalyst is selected from the group consisting of 5% platinum on charcoal, platinum oxide and Raney nickel.

7. The process according to claim 6 wherein said hydrogenation catalyst is 5% platinum on charcoal.

8. The process according to claim 7 wherein said hydrogenation reaction is carried out at room temperature.

9. A process for the synthesis of a compound of the formula

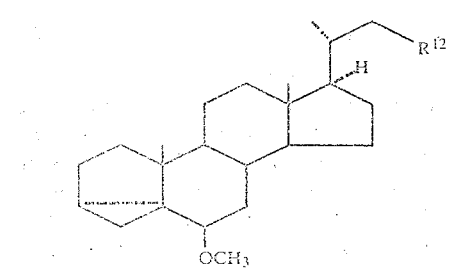

wherein $R^{12}$ is hydroxy,
which process comprises the steps of
a. reacting a compound of the formula

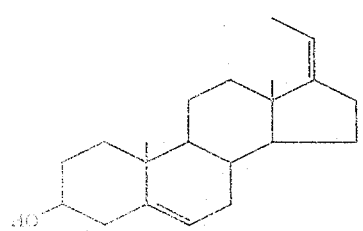

with a compound which will produce a compound of the formula

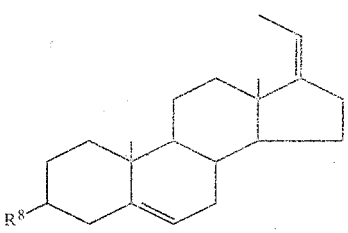

wherein $R^8$ is selected from the group consisting of halide, lower alkylsulfonyloxy and arylsulfonyloxy;

b. reacting the reaction product of step a. with formaldehyde or a compound capable of generating formaldehyde in situ in an inert solvent at temperatures ranging from $-20°$ to $45°$ C. in the presence of Lewis or protic acids to yield a compound of the formula

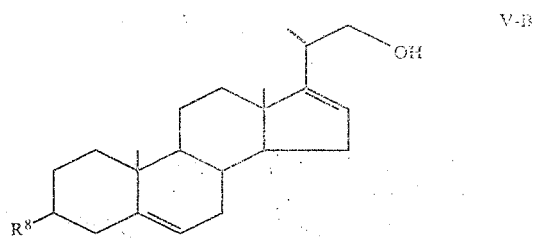

wherein $R^8$ is a conventional leaving group;

c. treating the reaction product of step b. with weak base in the presence of methanol at reflux temperatures to yield a compound of the formula

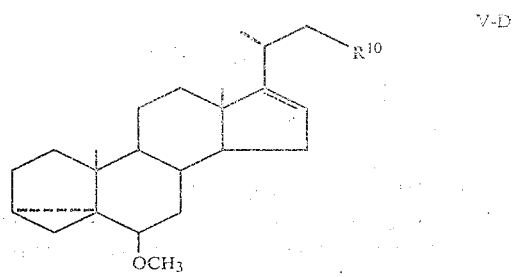

wherein $R^{10}$ is hydroxy;

d. reacting the reaction product of step c. with hydrogen in an inert solvent in the presence of a hydrogenation catalyst at temperatures ranging from $0°$ to $40°$ C. to yield a compound of the formula

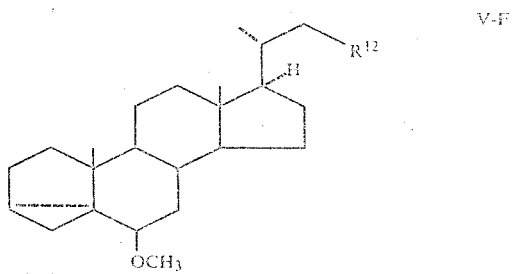

wherein $R^{12}$ is hydroxy.

10. A process for the synthesis of a compound of the formula

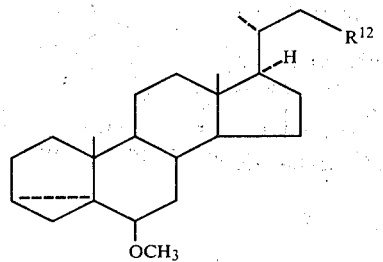

wherein $R^{12}$ is acyloxy,
which process comprises the steps of
a. reacting a compound of the formula

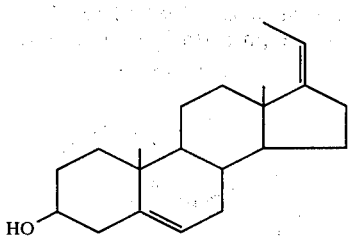

with a compound which will produce a compound of the formula

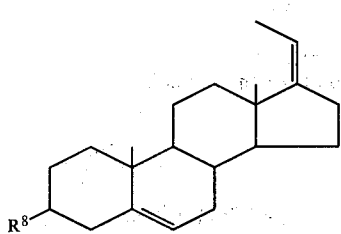

wherein $R^8$ is selected from the group consisting of halide, lower alkylsulfonyloxy and arylsulfonyloxy;

b. reacting the reaction product of step a. with formaldehyde or a compound capable of generating formaldehyde in situ in the presence of an acylating agent in an inert solvent at temperatures ranging from $-20°$ to $45°$ C. in the presence of Lewis or protic acids to yield a compound of the formula

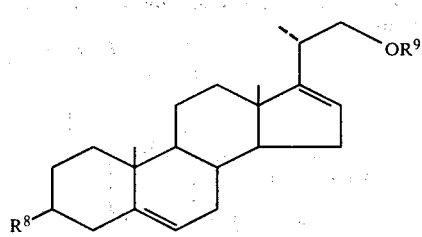

wherein $R^8$ is a conventional leaving group; and $R^9$ is acyl;

c. treating the reaction product of step b. with weak base in methanol at reflux temperatures to yield a compound of the formula

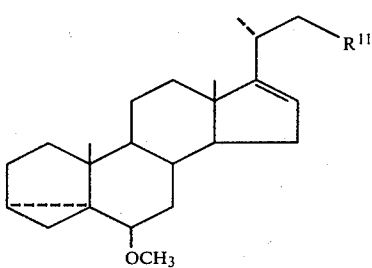

wherein $R^{11}$ is acyloxy;

d. reacting the reaction product of step c. with hydrogen in an inert solvent in the presence of a hydrogenation catalyst at temperatures ranging from $0°$ to $40°$ C. to yield a compound of the formula

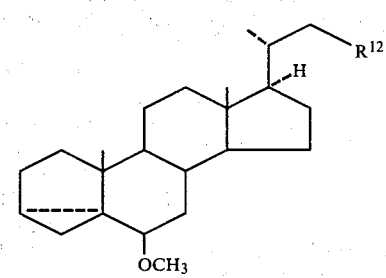

wherein $R^{12}$ is acyloxy.

11. The process of claim 9 or 10 wherein said leaving group is selected from the group consisting of lower alkylsulfonyloxy and arylsulfonyloxy.

12. The process of claim 9 or 10 wherein said leaving group is paratoluenesulfonyloxy.

13. The process of claim 9 or 10 wherein said Lewis or protic acids are selected from the group consisting of boron trifluoride etherate, aluminum chloride, methanesulfonic acid and trifluoroacetic acid.

14. The process of claim 9 or 10 wherein said Lewis acid is boron trifluoride etherate.

15. The process of claim 9 or 10 wherein said formaldehyde-producing compound is paraformaldehyde.

16. The process of claim 9 or 10 wherein said hydrogenation catalyst is selected from the group consisting of 5% platinum on charcoal, Raney nickel and platinum oxide.

17. The process of claim 9 or 10 wherein said hydrogenation catalyst is 5% platinum on charcoal.

18. The process of claim 9 or 10 wherein said weak base is pyridine.

19. The compound (Z)-1α,3β-pregna-5,17(20)-diene-1,3-diol as characterized by the formula

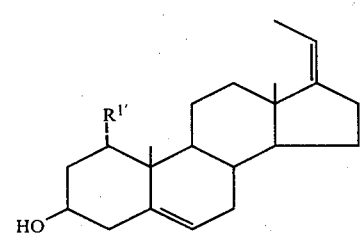

wherein $R^{1'}$ is hydroxy.

20. A compound of the formula

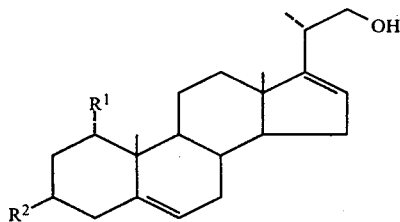

III wherein $R^1$ is hydrogen, hydroxy or acyloxy; and $R^2$ is hydroxy or acyloxy.

21. The compound of claim 20 wherein $R^1$ is hydrogen.
22. The compound of claim 21 which is (20S)-20-methylpregna-5,16-diene-3β,21-diol.
23. The compound of claim 21 which is (20S)-20-methylpregna-5,16-diene-3β,21-diol 3-acetate.
24. The compound of claim 20 wherein $R^1$ is hydroxy.
25. The compound of claim 24 which is (20S)-20-methylpregna-5,16-diene-1α,3β,21-triol.
26. The compound of claim 24 which is (20S)-20-methylpregna-5,16-diene-1α,3β,21-triol 3-acetate.
27. The compound of claim 20 wherein $R^1$ is acyloxy.
28. The compound of claim 27 which is (20S)-20-methylpregna-5,16-diene-1α,3β,21-triol 1-acetate.
29. The compound of claim 27 which is (20S)-20-methylpregna-5,16-diene-1α,3β,21-triol 1,3-diacetate.
30. The compound of claim 27 which is (20S)-20-methyl-1α,3β-ditrifluoroacetyloxypregna-5,16-diene-21-ol.
31. A compound of the formula

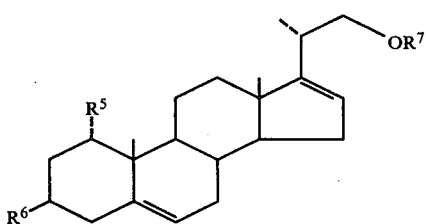

II-B wherein $R^5$ is hydrogen or acyloxy; $R^6$ is acyloxy; and $R^7$ is acyl.

32. The compound of claim 31 which is (20S)-20-methylpregna-5,16-diene-3β,21-diol diacetate.
33. The compound of claim 31 which is (20S)-20-methylpregna-5,16-diene-1α,3β, 21-triol 1,3,21-triacetate.

34. Compounds of the formula

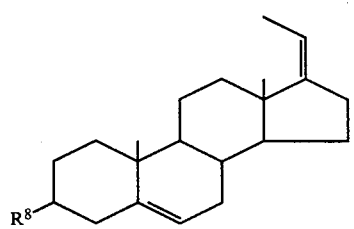

V-A wherein $R^8$ is selected from the group consisting of halide, lower alkylsulfonyloxy and arylsulfonyloxy.

35. The compound of claim 34 which is (Z)-pregna-5,17(20)-dien-3β-ol p-toluenesulfonate.

36. Compounds of the formula

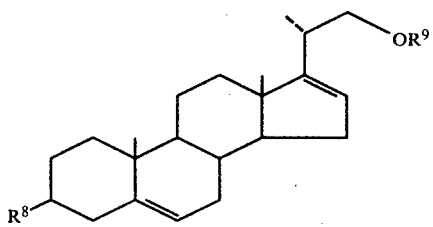

V-C wherein $R^8$ is selected from the group consisting of halide, lower alkylsulfonyloxy and arylsulfonyloxy; and $R^9$ is acyl.

37. The compound of formula 36 which is (20S)-20-methylpregna-5,16-dien-3,21-diol 21-acetate 3-p-toluenesulfonate.

38. The compound (20S)-3β,5α,6β-methoxy-20-methyl-3,5-cyclopregn-16-en-21-ol as characterized by the formula

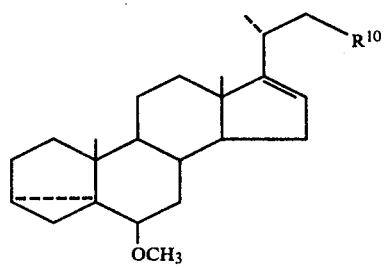

V-D wherein $R^{10}$ is hydroxy.

39. Compounds of the formula

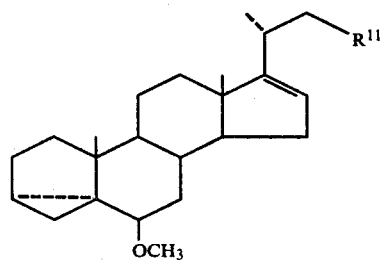

V-E wherein $R^{11}$ is acyloxy.

40. The compound of claim 41 which is (20S)-3β,5α,6β-methoxy-20-methyl-3,5-cyclopregn-16-en-21-ol acetate.

41. The compound (Z)-1α,3β-pregnene-5,17(20)-diene-1,3-diol 1,3-bistrifluoroacetate as characterized by the formula

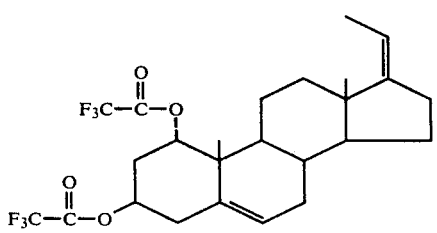

42. The process according to claim 8 wherein said acyloxy substituent is trifluoroacyloxy.

* * * * *